United States Patent

Crutchfield et al.

[11] 4,120,874
[45] Oct. 17, 1978

[54] DIESTERS OF 6-CYANO-2,2-TETRAHYDROPYRANDICARBOXYLATES

[75] Inventors: Marvin M. Crutchfield, Creve Coeur, Mo.; Kent P. Lannert, Freeburg, Ill.

[73] Assignee: Monsanto Company, St. Louis, Mo.

[21] Appl. No.: 756,946

[22] Filed: Jan. 5, 1977

[51] Int. Cl.² .................................. C07D 309/28
[52] U.S. Cl. .................. 260/345.8 R; 260/340.6; 260/347.4; 260/601 H; 260/615 A; 560/176; 560/180
[58] Field of Search ............... 260/345.8, 345.8 R

[56] References Cited
PUBLICATIONS
Chem. Abstracts: 85:21033h; 71:3209b; 57:13714b.

Primary Examiner—Ethel G. Love
Attorney, Agent, or Firm—S. M. Tarter; E. P. Grattan; F. D. Shearin

[57] ABSTRACT

A compound of the formula

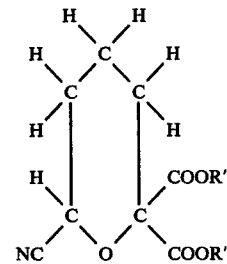

wherein R' is lower alkyl, is useful as an intermediate in the preparation of a corresponding tricarboxylate, which is a useful detergent builder.

1 Claim, No Drawings

DIESTERS OF 6-CYANO-2,2-TETRAHYDROPYRANDICARBOXYLATES

BACKGROUND OF THE INVENTION

The present invention relates to a process for preparing compounds of the molecular structure represented by the formula:

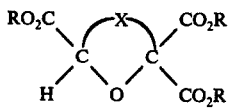

wherein X is selected from the group consisting of:
(a) where the compounds are tetrahydropyran type compounds

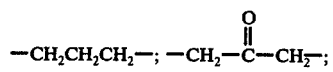

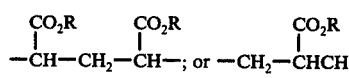

(b) where the compounds are 1,4-dioxane type compounds:

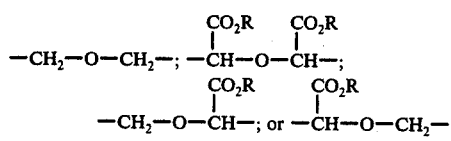

and
(c) where the compounds are tetrahydrofuran type compounds:

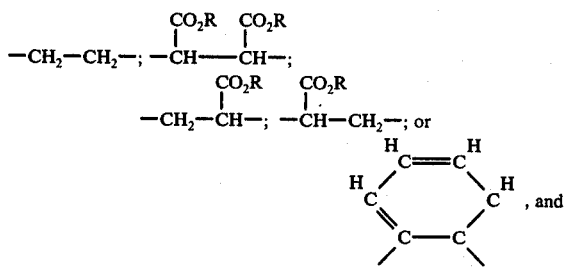

wherein R is selected from the group consisting of alkali metal, ammonium, trialkanolammonium, and lower alkyl, branched or straight chain, with up to about $C_{20}$ in the chain, comprising:
(a) preparing a suitable halo dicarboxy ester of an aldehyde of the general formula

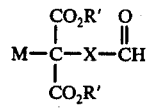

wherein M is halogen, X is as defined above, and R' is lower alkyl, preferably ethyl or methyl.
(b) cyclizing the compound of (a) to the cyclic cyano diester intermediate of the formula:

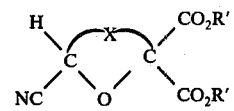

wherein X and R' are as given above, and
(c) hydrolyzing the intermediates to Step b) to the corresponding salts, and if desired, converting the salts to the corresponding triesters or acids.

The salt compounds produced in accordance with the process of the present invention have utility as water softeners, detergent builders, calcium and magnesium sequestrants, scale dissolvers, and the like. The compounds may be used alone or as additives to a variety of solid or liquid detergent formulations. In such formulations the compounds enhance the cleaning capacity of the detergent by providing a builder, threshold or other effect. The esters are useful in synthesizing the pure salt forms of the compounds. The cyclic cyano diester intermediates are useful in preparing the end product trisalts, esters or acids.

DESCRIPTION OF THE PRIOR ART

The preparation of some of the compounds within the scope of the general formula set forth above is described in U.S. patent application Ser. No. 756,947 filed Jan. 5, 1977 in the names of Marvin M. Crutchfield and Charles J. Upton. In that application the inventors describe a process for producing compounds, such as the trisodium and triester-2,2,6-tetrahydropyran-tricarboxylates by a process of basic carboxylation to produce the partial esters followed by hydrolysis to the salt forms. The salts in turn are capable of being esterified to the corresponding full esters.

The present invention comprises a novel and highly effective route to the synthesis of the subject compounds which is entirely dissimilar to the phenate carboxylation approach taken by Crutchfield and Upton.

SUMMARY OF THE INVENTION

The invention provides a highly effective method for synthesizing compounds having a molecular structure represented by the formula:

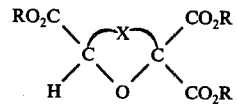

wherein X and R are as described above.

The method for preparing the subject compounds generally comprises,
(a) preparing a suitable halo dicarboxy ester of an aldehyde of the general formula

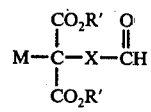

wherein M is halogen, and R' is lower alkyl, preferably ethyl or methyl.

(b) cyclizing the compound of a) to form the cyclic diester intermediate of the formula:

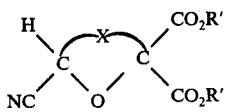

wherein X and R' are as described above, (c) hydrolyzing the intermediates of Step (b) to the corresponding salts, and (d) if desired, esterifying the salts of Step c) to the corresponding esters.

Among the preferred compounds (and intermediates) of the above general formula which may be prepared in accordance with the present process, are the following:

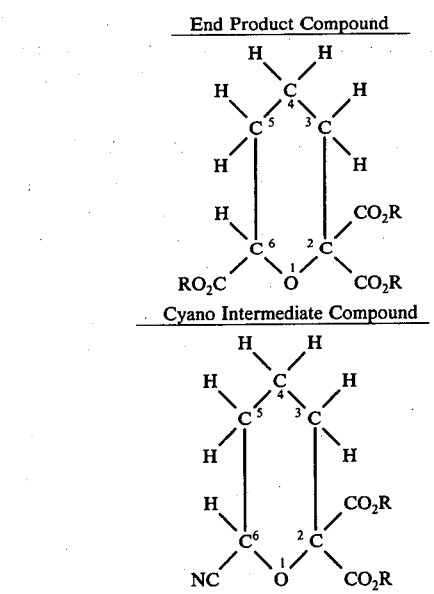

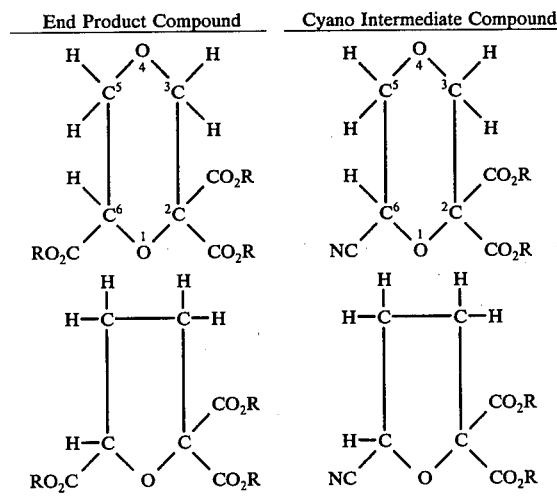

In the above formulae R is as described above, but is preferably $CH_3$ or $C_2H_5$ for the cyano intermediate compound and H, Na, $CH_3$ or $C_2H_5$ for the end product compound.

DETAILED DESCRIPTION OF THE INVENTION

A detailed description of the process of the present invention is embodied in the following illustrative working examples.

EXAMPLE 1

Preparation of Trisodium 2,2,6-Tetrahydropyrantricarboxylate (a) Preparation of γ-Chlorobutyraldehyde Diethyl Acetal The named compound was prepared by the method of Loftfield, J. Am. Chem. Soc., 73 1365 (1951), with minor modifications, according to the following general reactions:

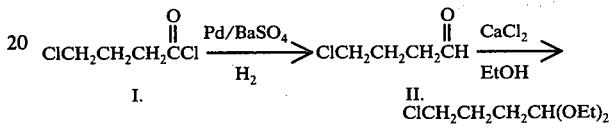

In carrying out this step of the preparation a 3l baffled 3-neck, round bottom flask was fitted with a gas dispersion tube, mechanical stirrer and reflux condenser. The flask was charged with 282g (2 moles) of γ-chlorobutyryl chloride, 1450 ml toluene, 30g of 5% Pd/BaSO₄, and 3.1 ml of quinoline/sulfur catalyst poison (catalyst poison was prepared by refluxing 1g sulfur with 6g quinoline for 5 hours and diluting to 70 ml with xylene). Hydrogen was then bubbled through the stirred reaction mixture and the temperature raised to reflux. The off-gases were bubbled into a 2l flask containing 1.5l water. 5N NaOH was added to neutralize the HCl as it was given off. After 3 hours, HCl evolution had stopped and the reaction mixture was allowed to cool at room temperature under a $N_2$ atmosphere.

A solution of 200g $CaCl_2$ in 1250 ml abs. EtOH was added and the stirring was continued overnight. The reaction mixture was filtered to remove the catalyst and the filtrate was washed with 800 ml water and 2 × 400 ml 5% $NaHCO_3$ solution. The aqueous phases were combined and extracted with 500 ml toluene. The organic phases were combined and washed with 400 ml 5% $NaHCO_3$, 400 ml saturated NaCl and dried over anhydrous $K_2CO_3$. The mixture was filtered and the bulk of the toluene was removed on a rotary evaporator. The crude product was then distilled through an 18 inches silvered vacuum jacketed column packed with Berl saddles. The product (283g) was collected at 83°-4° at water aspirator pressure (89°-92°/14mm). This is a 78% yield based on raw materials. A later similar run gave 81%. ¹H nmr was consistent with the structure.

(b) Preparation of δ,δ-Dicarbethoxyvaleraldehyde Diethyl Acetal

The named compound was prepared by reacting the γ-chlorobutyraldehyde diethyl acetal prepared in accordance with Step a), above, with sodium diethyl malonate according to the following reaction:

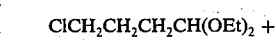

III.

-continued

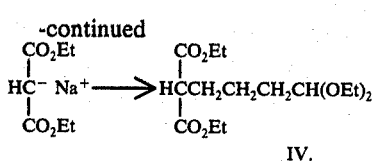

IV.

To carry out the foregoing preparation 168g (1.05 mole of diethyl malonate and 15g (0.1M) NaI were added to a solution of 23g (1M) of Na and metal dissolved in 750 ml ethanol. After about 5 minutes at 50° C., 190g (1.05M) of γ-chlorobutyraldehyde diethyl acetal was added. The temperature was raised to reflux and after 1.5 hours an additional 80g (0.5M) of diethyl malonate was added. The reaction mixture was refluxed overnight. The next day glc indicated unreacted acetal, so additional Na/EtOH was added and the mixture was refluxed for 3 more hours. The ethanol was then removed on a rotary evaporator and the residue taken up in a mixture of 200 ml $H_2O$ and 200 ml ether. The layers were separated and the ethereal layer was washed with 2 × 200 ml 5% $NaHCO_3$. The aqueous washes were combined with the original aqueous layer and extracted with 200 ml ether. The ethereal solutions were combined and washed with 5% $NaHCO_3$ and saturated NaCl. After drying over $K_2CO_3$ and removing the ether on a rotary evaporator, 366g of 60–70% pure product remained.

This crude product was distilled under vacuum and the product collected at 115°–124° at 0.1mm Hg. The product (223g, 70% yield) gave a 'H nmr consistent with the structure.

(c) Preparation of δ-Bromo-δ,δ-Dicarbethoxyvaleraldehyde Diethyl Acetal

The named compound was prepared by reacting δ,δ-dicarbethoxyvaleraldehyde diethyl acetal as prepared in Step b) with sodium ethoxide and then reacting the resulting sodium compound with bromine according to the following reactions:

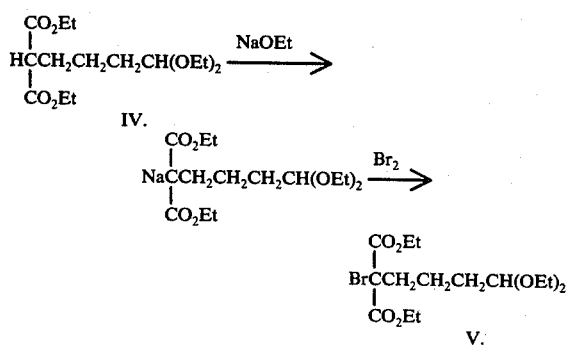

These reactions were carried out in the following manner:

To a slurry of 45g 50% NaH (washed with 4 × 100 ml pentane) in 750 ml DMF was added 259g of the diethyl acetal of Step b) and 4.5 ml ethanol. The mixture was stirred at <25° for 2 hours and then an additional 4.5 ml EtOH was added. Since this caused increased $H_2$ evolution, the mixture was stirred an additional 6 hours, after which 9 more ml of EtOH were added. The reaction mixture was cooled to about 10° and a solution of 144g $Br_2$ in 200 ml DMF was added while the temperature was maintained at <15°. The reaction mixture was allowed to stir overnight at room temperature.

The reaction mixture was diluted with 1l of $H_2O$ and extracted with 3 × 1l benzene. The benzene extracts were washed with 2 × 1l $H_2O$ and 2 × 1l saturated NaCl. The benzene was removed on a rotary evaporator leaving 135g crude product which by glc was about 85% pure. The 'H nmr was in agreement with the structure. Experience with a previous run had shown that decomposition occurred during distillation so this material was used without further purification.

The choice of DMF as a solvent for this step was not optimum since DMF reacts with NaOEt as evidenced by the presence of considerable amounts of dimethyl amine at the time of the $Br_2$ addition.

(d) Preparation of δ-Bromo-δ,δ-Dicarbethoxyvaleraldehyde

The named compound was prepared by the hydrolysis of the diethyl acetal prepared in accordance with Step (c), above, by the following reaction:

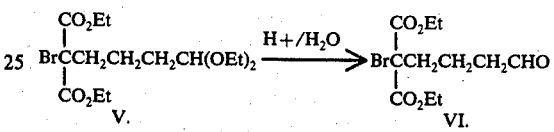

In this step a solution of 305g of crude diethyl acetal in 300 ml benzene was stirred overnight at room temperature with 2.5l of 4N HCl. The reaction mixture was extracted with 5 × 500 ml benzene. The benzene extracts were washed with 1 × 500 ml $H_2O$, 2 × 500 ml 5% $NaHCO_3$, and 2 × 500 ml saturated NaCl. The solution was dried over $CaSO_4$ and the benzene removed on a rotary evaporator having 240g of crude product. The 'H nmr was consistent with the structure. The material was used without further purification.

(e) Preparation of Diethyl 6-cyano-2,2-tetrahydropyran dicarboxylate

The named compound was prepared by cyclizing the aldehyde prepared in accordance with Step d) supra, using sodium cyanide in dimethyl sulfoxide according to the following reaction:

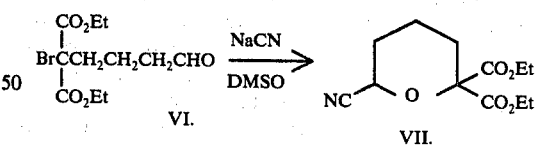

To a slurry of 50g of NaCN in 700 ml DMSO was added 222g crude aldehyde in 80 ml DMSO. The temperature rose spontaneously to 65° at which it was held by controlling the rate of addition of VI. The temperature was then held at 65° for an additional 4 hours.

The reaction mixture was diluted with 1.5l $H_2O$ and extracted with 6 × 500 ml benzene. The combined extracts were washed with 500 ml saturated $NaHSO_3$, 2 × 500 ml 5% $NaHCO_3$, 3 × 500 ml saturated NaCl and then dried over $CaSO_4$. The benzene was removed on a rotary evaporator having 145g crude product about 50–55% pure.

After several vacuum distillations 65g of 98% pure product was obtained. B.p. 119–121 mm Hg. The 'H nmr was consistent with the structure.

(f) Preparation of Trisodium 2,2,6-Tetrahydropyrantricarboxylate

The named compound was prepared by hydrolysis of the 6-cyano-2,2-tetrahydropyrandicarboxylate prepared in accordance with Step (e) above, by the following reaction:

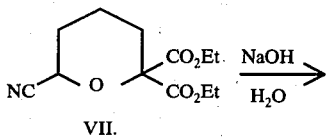
VII.

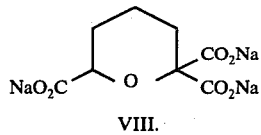
VIII.

To a solution of 81g of 50% NaOH and 80 ml H$_2$O still warm from mixing was added a solution of 65g of VII in 200 ml MeOH. After stirring overnight at room temperature the solution was warmed to insure that ammonia evolution had ceased. When no ammonia could be smelled, the solution was allowed to cool and stand overnight at room temperature. This solution was poured into MeOH and an oil was obtained which solidified on further treatment with MeOH as the trisodium salt.

(g) Preparation of Triethyl 2,2,6-Tetrahydropyrantricarboxylate (IX)

The named compound was prepared by esterification of the trisodium salt of Step (f). The salt was added to a solution of 600 ml of ethanol and 160 ml acetyl chloride and refluxed for 3 hours. The excess HCl was neutralized by adding solid NaHCO$_3$ and water until CO$_2$ evolution ceased. Additional H$_2$O was added until almost all of the solids had dissolved. The aqueous solution was then extracted with 3 × 500 ml benzene. The extracts were washed with 300 ml 5% NaHCO$_3$ and 2 × 300 ml saturated NaCl and filtered. Most of the benzene was removed on a rotary evaporator and the residue dried over CaSO$_4$. The remaining benzene was removed and the residue (50g) was found to be 95% pure. This was vacuum distilled to give a 30.6g fraction which was 97% pure. Other fractions of 93–95% purity were also obtained but not combined with the purest cut. The 'H nmr and IR were identical to those obtained for material prepared by the phenate carboxylation route employed by Crutchfield and Upton and described in previously identified Application Serial No.

EXAMPLE 2

Ammonium, triethanolamine, other soluble alkali metal salts, and the acid form of the cyclic tricarboxylate conpounds of this invention are prepared by passing an aqueous solution of the corresponding sodium salt through a column of cationic exchange resin charged with the desired cation, followed by isolation of the salt from the aqueous solution by evaporation or crystallization.

EXAMPLE 3

The trisodium 2,2,5-tetrahydrofurantricarboxylate may be prepared as follows:

(a) Preparation of γ,γ-dicarbethoxybutyraldehyde

First, 100 ml acrolein was added to a solution of 180g diethyl bromomalonate, 14g tributylamine, and 600 ml ethanol while cooling in an ice bath. After 2–3 hours, an additional 1.5g tributylamine and 20 ml acrolein was added. The stirring was continued for an additional 1 to 2 hours without additional cooling. The reaction mixture was neutralized with 7 ml glacial acetic acid and the ethanol and unreacted acrolein were removed on a rotary evaporator. The residue was diluted with 500 ml benzene and washed with 3 × 100 ml H$_2$O and 2 × 100 ml saturated NaCL solution. The benzene solution was dried over CaSO$_4$ and rotary evaporated to yield 207g of yellow oil which was indicated to be 48% product by glc.

(b) Preparation of 4-cyano-2,2-dicarbethoxytetrahydrofuran

To a slurry of 30g of NaCN in 500 ml dimethylsulfoxide (DMSO) was added a solution of 150g of the crude bromoaldehyde product of Step a) in 100 ml DMSO. The reaction was exothermic and cooling was required to maintain the temperature below 70° during addition. After the addition was complete heating was required to maintain the temperature at 60°–70° for 3.5 hours. The reaction mixture was allowed to cool to room temperature and then was poured into 600 ml H$_2$O. This solution was extracted with ether. The ethereal extracts were combined, washed with water and saturated NaCl, and dried over CaSO$_4$. After removing the ether on a rotoevaporator 87.3g of red brown oil remained which contained 91% product by glc. Vacuum distillation (120°–150°/0.05 mm Hg) gave the product as a colorless oil. 'Hnmr analysis was consistent with the structure.

(c) Preparation of Trisodium 2,2,5-Tetrahydrofurantricarboxylate

To a warm solution of 64.1g of 50% NaOH in 200 ml H$_2$O was added 60g of the product of Step b) diluted with 20 ml ethanol. The solution was initially two phase but became homogeneous after stirring several minutes. The solution was maintained at 60°–70° under a stream of N$_2$ for 3 hours. The resulting yellow solution was poured into 450 ml MeOH. An oil formed which on further workup under MeOH gave a yellow solid. The solid was dissolved in H$_2$O and treated twice with charcoal. The pale yellow solution was treated repeatedly with ethanol until it solidified. The solid was washed with ether and dried overnight in a vacuum oven at 80°. The solid was ground in a blender and dried an additional 3 hours in the vacuum oven. The yield was 59g of off-white powder.

'Hnmr indicates some ethanol was still present as well as ½ mole H$_2$O. Thermographic analysis showed a 5.9% weight loss up to 350° at which point decomposition occurred. There appears to be a very thermally stable ½ hydrate which does not break down until about 250°. Glc analyses of the salt indicated 84% of the trisodium 2,2,5-tetrahydrofurantricarboxylate and 15% dicarboxylate. Dicarboxylate probably resulted from decarboxylation of some of the tricarboxylate during hydrolysis and/or charcoal treating. The divalent ion electrode titration gave the following values: A = 54 mV; B = 37 mV; C = 6.2 ml; D = 7.4 ml for an intensity-capacity index of 92% STP.

The salt appears to have a water solubility of slightly greater than 50% and when a 50% solution is allowed to evaporate, crystals of the product form. The solution could be evaporated to dryness and the product did not appear to be hydroscopic. Purification by crystallization should be possible.

EXAMPLE 4

Preparation of Trisodium 1,4-Dioxane-2,2,6-tricarboxylate

Trisodium 1,4-dioxane-2,2,6-tricarboxylate and its esternitrile precursor is prepared in the same manner as described in Example 1 for trisodium 2,2,6-tetrahydropyrantricarboxylate except that Compound X:

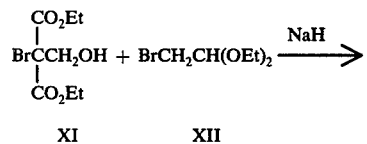
X is substituted for Compound V in Step (d) of Example 1. Compound X is prepared as follows:

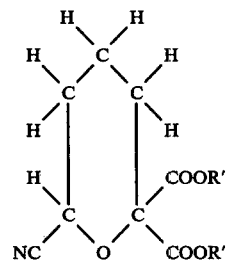

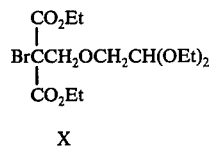
X

A solution of 27g of (I) as described in A. Ya. Yakubovich and I. N. Belyreva, Zhur, Obshchei Khim. 31, 2119–22 (1961) CA: 56, 313e (1962) in 25 ml tetrahydrofuran (THF) is added to a slurry of 2.4g of NaH in 100 ml THF. When evolution of $H_2$ has ceased, 19.7g of II is added and the mixture solution warmed to reflux temperature of the THF. The reaction mixture is refluxed until neutral. The solvent is removed on a rotary evaporator. The residue is taken up in ether, washed with water and saturated NaCl solution and dried over $CaSO_4$. The ether is removed on a rotary evaporator leaving the crude product.

What is claimed is:

1. A compound of the formula

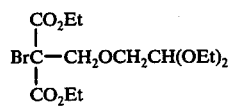

wherein R' is lower alkyl.

* * * * *